United States Patent [19]
Yamaguchi

[11] Patent Number: 4,840,181
[45] Date of Patent: Jun. 20, 1989

[54] SPHYGMOMANOMETER ADOPTING RECOGNITION OF KOROTKOFF SOUNDS

[75] Inventor: Keiji Yamaguchi, Shimizu, Japan
[73] Assignee: Terumo Corporation, Tokyo, Japan
[21] Appl. No.: 32,555
[22] Filed: Apr. 1, 1987
[30] Foreign Application Priority Data
   Apr. 3, 1986 [JP]  Japan .................. 61-75452
[51] Int. Cl.$^4$ ............................. A61B 5/02
[52] U.S. Cl. .................. 128/680; 128/681
[58] Field of Search .............. 128/672, 677–686
[56] References Cited

U.S. PATENT DOCUMENTS

| | | | |
|---|---|---|---|
| 4,313,445 | 2/1982 | Georgi | 128/682 X |
| 4,418,700 | 12/1983 | Warner | 128/672 X |
| 4,476,876 | 10/1984 | Uchiyama | 128/682 |
| 4,501,281 | 2/1985 | Furukawa et al. | 128/680 |
| 4,549,549 | 10/1985 | Furukawa | 128/680 |
| 4,592,366 | 6/1986 | Sainomoto et al. | 128/680 |
| 4,677,983 | 7/1987 | Yamaguchi et al. | 128/680 |
| 4,768,519 | 9/1988 | Yamaguchi | 128/680 |

FOREIGN PATENT DOCUMENTS 3041139 5/1982 Fed. Rep. of Germany ...... 128/680

*Primary Examiner*—Kyle L. Howell
*Assistant Examiner*—Angela D. Sykes
*Attorney, Agent, or Firm*—Staas & Halsey

[57] ABSTRACT

A sphygmomanometer includes a pump for applying variable pressure to a blood vessel, a microphone for sensing oscillation which is produced from the blood vessel being pressurized by the pump, a pressure detecting section for sensing the pressure being applied to the blood vessel, and a Korotkoff sound recognizing section for recognizing Korotkoff sounds out of the oscillation detected by the microphone. When the recognizing section has recognized a Korotkoff sound, the instantaneous pressure on the blood vessel is detected by the pressure detecting section to measure blood pressure. Recognition of Korotkoff sounds by the recognizing section is inhibited until a predetermined period of time expires since the recognition of a Korotkoff sound, to prevent the tailing of a Korotkoff sound from being recognized erroneously.

8 Claims, 9 Drawing Sheets

SPHYGMOMANOMETER ADOPTING RECOGNITION OF KOROTKOFF SOUNDS

BACKGROUND OF THE INVENTION

1. Field of the Invention

The present invention relates to a stethoscopic sphygmomanometer and, more particularly, to a stethoscopic sphygmomanometer capable of recognizing the tapping sounds of arterial blood flow, or so-called Korotkoff sounds, in distinction from noise.

2. Description of the Related Art

In the stethoscopic measurement of blood pressure, pressure applied from an inflated cuff to a blood vessel is varied while, at the same time Korotkoff tapping sounds from the blood vessel are recognized to determine systolic and diastolic pressures.

A filter and comparator system is an approach heretofore proposed for the recognition of Korotkoff sounds out of an output signal of a microphone, which is fitted on an inflated cuff.

As generally accepted in the art, the spectral distribution of Korotkoff tapping sounds is distinguishable in frequency distribution from physical movements and externally derived noise. The filter and comparator system is derived from the above distinction and constructed such that a signal sensed by a microphone which is attached to an inflated cuff is passed through a filter to reduce the amplitude of any frequency component other than Korotkoff sounds and, then, the frequency component of Korotkoff sounds is compared with a predetermined threshold by a voltage comparator so as to determine a relationship therebetween.

However, difficulty has been experienced with the filter and comparator system for various reasons in extracting only Korotkoff sounds which is free from noise. Namely, the frequency component of Korotkoff sounds is dependent not only upon the individual but also upon the time of the measurement, cuff pressure and other various conditions of measurement. The frequency component of noise extends over a wide range, i.e., several tens to several hundreds of hertz overlapping the frequency component of Korotkoff sounds and, in addition, the waveform pattern of noise is in many cases analogous to that of Korotkoff sounds.

Another problem with the filter and comparator system is that Korotkoff sounds cannot be easily distinguished from pulse sounds when the frequency component of the former is comparatively low and, because the discrimination is performed in terms of level, the accuracy of measurement is apt to be affected by differences in the amplitude of Korotkoff sounds.

While another recognition system which is based on the waveform of Korotkoff sounds (pattern recognition system) is also known in the art, it still fails to readily identify Korotkoff sounds in distinction from noise because Korotkoff sounds and noise resemble each other with regard to waveform pattern.

Especially, immediately after the recognition of a Korotkoff tapping sound by pattern recognition, noise which is lower in amplitude than and similar in pattern to Korotkoff sounds, i.e., tailing or hangover of Korotkoff sound is sometimes recognized as a Korotkoff sound. This is ascribable partly to the fact that the amplitude of Korotkoff sounds depends upon the individual, and partly to the fact that with regard to the same person the amplitudes of Korotkoff sounds just after the start of measurement and just before the end of measurement are sometimes far smaller than the largest amplitude reached during the course of measurement. The tailing of Korotkoff sounds tends to become longer as the amplitude of Korotkoff sound becomes greater while the duration of such tailing depends upon the amplitude of Korotkoff sound, adding to the difficulty of noise removal.

SUMMARY OF THE INVENTION

It is therefore an object of the present invention to provide a sphygmomanometer which is capable of recognizing Korotkoff sounds accurately without recognizing the tailing of Korotkoff sound as a true Korotkoff sound.

In order to achieve the above object, a sphygmomanometer of the present invention includes pressurizing means for applying variable pressure to a blood vessel, oscillation detecting means for detecting sound or oscillation produced from the blood vessel being pressurized by the pressurizing means, pressure detecting means for detecting pressure being applied to the blood vessel, Korotkoff sound recognizing means for recognizing Korotkoff sounds out of the oscillation detected by the oscillation detecting means, blood pressure computing means for computing blood pressure from the pressure being applied to the blood vessel and detected by the pressure detecting means when a Korotkoff sound is recognized by the Korotkoff sound recognizing means, and time width setting means for setting a predetermined time width based on the Korotkoff sound which is detected by the Korotkoff sound recognizing means and inhibiting an output from the oscillation detecting means to the Korotkoff sound recognizing means for that period of time. After the recognition of a Korotkoff sound, the Korotkoff sound recognizing means does not perform recognition of Korotkoff sounds until the period of time set up by the time width setting means expires.

One of the characteristic features of the present invention is that the time width setting means is capable of setting a time width which matches with the amplitude of a Korotkoff sound recognized immediately before by the Korotkoff sound recognizing means.

The Korotkoff sound recognizing means may be constructed to hold a signal waveform which is detected by the oscillation sensing means, detect a maximum point $C_3$ of the waveform held, detect a point of minimum value $C_2$ within a predetermined time slot $t_1$ the end of which is the maximum point $C_3$, decide whether a level differential between the points $C_2$ and $C_3$ detected lies in a predetermined range, when decided that it lies in the predetermined range, detect a point of largest value $C_1$ within a predetermined time slot $t_2$ the end of which is the point $C_2$, decide whether a level differential between the points $C_1$ and $C_2$ detected lies in a predetermined range, when decided that it lies in the predetermined range, detect a point of smallest value $C_4$ within a predetermined time slot $t_3$ the beginning of which is the point $C_3$, and decide whether a level difference between the points $C_4$ and $C_3$ lies in a predetermined range, thereby recognizing a Korotkoff sound in a signal waveform.

BRIEF DESCRIPTION OF THE DRAWINGS

The above and other objects, features and advantages of the present invention will become more apparent from the following detailed description taken with the accompanying drawings in which.

DESCRIPTION OF THE PREFERRED EMBODIMENT

Figure 2:
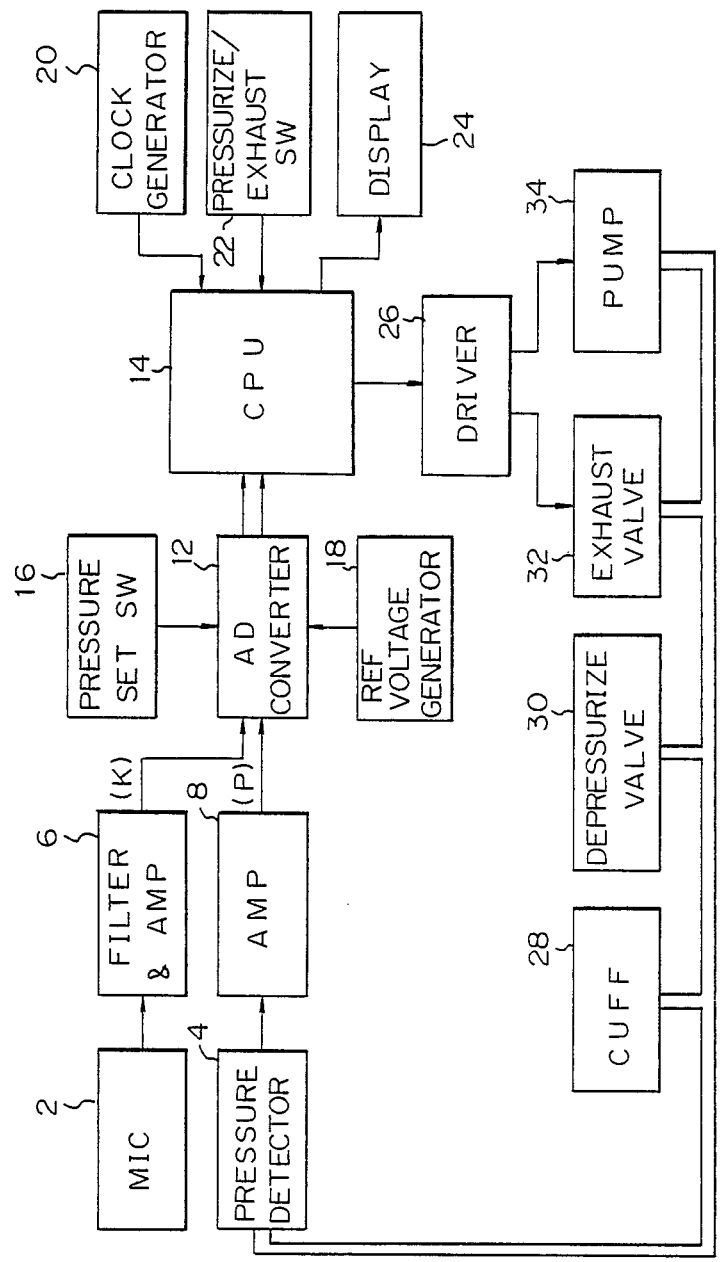
FIG. 2 is a block diagram showing the hardware arrangement of the sphygmomanometer of the present invention.

Referring to FIG. 2, the hardware of a sphygmomanometer in accordance with the present invention is shown. As shown, the sphygmomanometer includes a microphone 2 adapted to sense sound or oscillation from a blood vessel and convert it into an electrical signal for the detection of Korotkoff sounds. Korotkoff sounds issue from an artery which is pressurized by an inflated cuff 28 and then sequentially depressurized. The blood pressure at which the first Korotkoff sound is generated is referred to as systolic pressure while the blood pressure at which the last Korotkoff sound is generated is referred to as diastolic pressure.

Figure 3A:
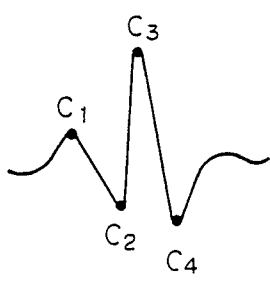
FIGS. 3A and 3B are views each showing a characteristic pattern of a Korotkoff sound waveform.
Figure 3B:
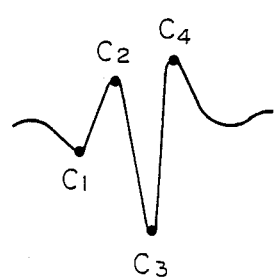

FIGS. 3A and 3B show patterns which are particular to Korotkoff tapping sounds. Specifically, FIG. 3A shows a typical pattern of Korotkoff sounds to which the sphygmomanometer is responsive, and FIG. 3B shows an inverted version of the pattern of FIG. 3A with respect to signal level. A Korotkoff sound is characterized by four discrete points, or characterizing points, $C_1$, $C_2$, $C_3$ and $C_4$, as shown in FIGS. 3A and 3B. The sphygmomanometer of the present invention is constructed to recognize a Korotkoff sound on the basis of a relationship between the four characterizing points $C_1$ to $C_4$. The point $C_3$ is generally referred to as a peak where the signal level is highest (FIG. 3A) or a bottom where it is lowest (FIG. 3B), playing a significant role for the recognition of Korotkoff sounds as will be described. Once the characterizing point $C_3$ is determined, the other characterizing points $C_1$, $C_2$ and $C_4$ can each be determined by a predetermined analytical procedure starting from the point $C_3$.

A Korotkoff sound is extracted from an output signal of the microphone 2 by a method which will be described in detail later.

A filter and amplifier 6 shapes the waveform of and amplifies the output signal of the microphone 2 to produce a signal K which is applied to an analog-to-digital (AD) converter 12. A pressure detector 4 serves to detect instantaneous pressure which is applied from an inflated cuff 28 to a blood vessel by a pressurizing means, while converting the detected pressure into an electrical signal. An amplifier 8 amplifies an output signal of the pressure detector 4 to produce a signal P which is representative of the pressure being applied to the blood vessel. The signal is also fed to the AD converter 12. The signals K and P which are analog signals and supplied from a filter and amplifier 6 or amplifier 8 are individually turned into digital signals by the AD converter 12. Reference voltage is fed from a reference voltage source 18 to the AD converter 12 so that the converter 12 may convert each of the signals K and P into a digital signal having, for example, 256 consecutive steps. A pressure setting switch 16 is a switch accessible for manually setting up a certain pressure such as 120 mmHg, 150 mmHg, 180 mmHg or 210 mmHg referencing usual systolic pressure of a subject. The switch 16, therefore, prevents the maximum pressure applied to the blood vessel from the cuff 28 at the beginning of measurement from being elevated to an excessive degree.

The signals K and P which are outputted by the AD converter 12 are routed to and stored in a central processing unit (CPU) 14. Processing the signals K and P as described later, the CPU 14 identifies Korotkoff tapping sounds.

A clock generator 20 functions to generate a clock signal which is fed to the CPU 14 for controlling its operation timings. A driver 26 selectively drives a pump 34 and a valve 32 in response to a command from the CPU 14. While the pump 34 is adapted to feed air under pressure to inflate the cuff 28 and, thereby, pressurize a blood vessel, the valve 32 is adapted to exhaust the cuff 28 of the air when it is desired to stop the measurement. Another valve 30 is provided for sequentially discharging the compressed air which is fed from the pump 34 to the cuff 28, thereby depressurizing the cuff 28 little by little during measurement. The pump 34 and the valve 32 are selectively driven by a pressurize/exhaust switch 22. The reference numeral 24 designates a display which serves multiple functions, e.g., displaying values as measured by the CPU 14 and alerting the operator to the end of measurement as well as to various conditions of the device by use of a buzzer and others.

Figure 1:
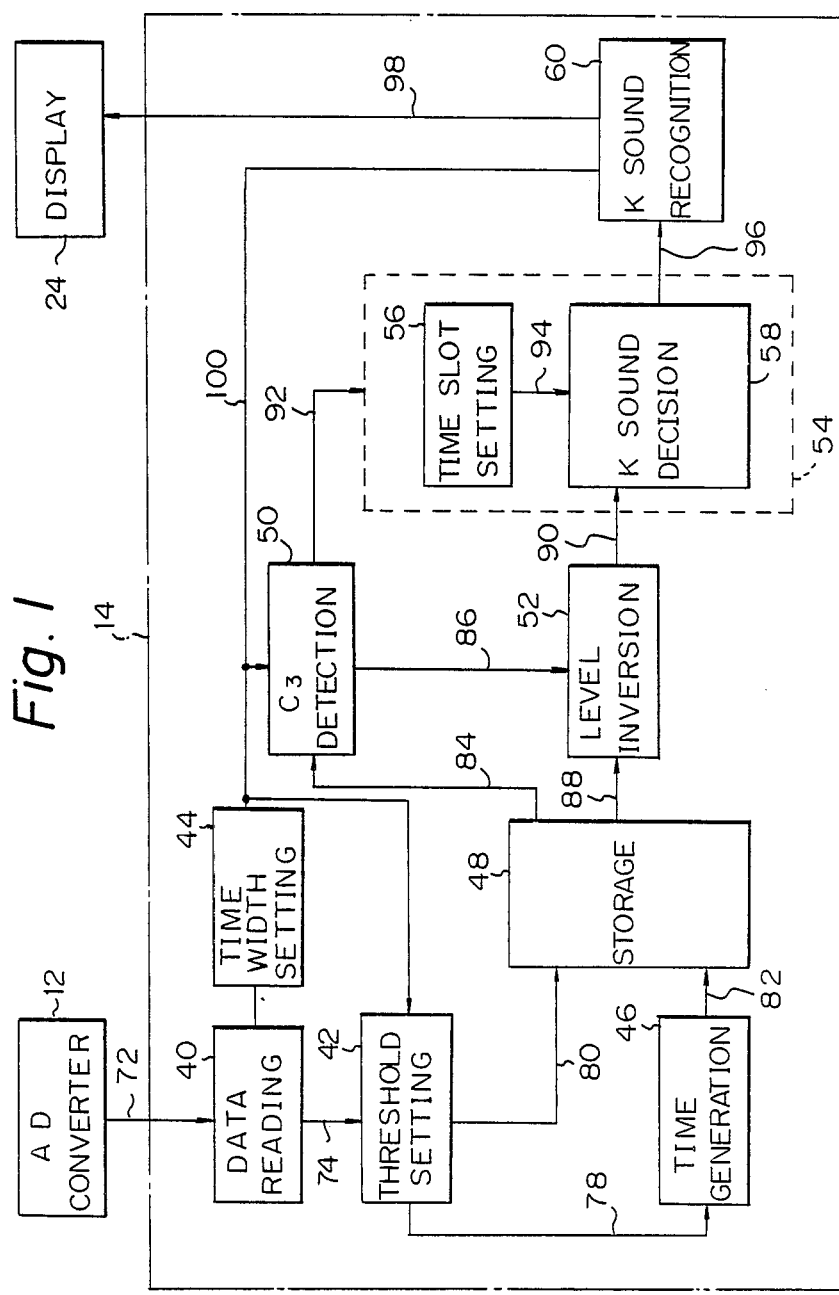
FIG. 1 is a block diagram showing various functions of a central processing unit (CPU) which is included in a sphygmomanometer in accordance with the present invention.

Referring to FIG. 1, various functions which are implemented with a program within the CPU 14 are shown in a block diagram. A data reading section 40 reads in the digital signals which are outputted by the AD converter 12. A time width setting section 44 sets up a certain time width on the basis of the amplitude of a Korotkoff sound which was recognized by immediately preceding processing, which will be described, and inhibits the output of the data reading section 40 for that period of time. A threshold setting section 42 sets up a certain threshold value according to the magnitude of a Korotkoff sound which was recognized by immediately preceding processing. A time generating section 46 generates time information. A storage 48 is adapted to store a sound data signal of the instant when the peak or the bottom is detected, together with time information of that instant. The storage 48 may advantageously be implemented with a random access memory (RAM). A $C_3$ detecting section 50 is provided for detecting the maximum or the minimum value of sound data which are read out of the storage 48. A level inverting section 52 inverts the levels of signal waveform data which are read out of the storage 48 for the recognition of Korotkoff sounds, according to requirement. A characterizing point detecting section 54 performs predetermined calculations with signal waveform data and time data which are read out of the storage 48, thereby deciding whether or not a waveform having the characterizing points $C_1$, $C_2$ and $C_4$ is present. The section 54 consists of a subsection 56 for generating predetermined time slot data, and a subsection 58 for determining whether or not sound data of characterizing signal levels are present. When the $C_3$ detecting section 50 delivers a signal to the characterizing point detecting section 54 informing it of the detection of the point $C_3$, the section 54 detects the respective characterizing points according to a predetermined calculating procedure. A K (Korotkoff) sound recognizing section 60 functions to identify a Korotkoff sound by examining a relationship between the characterizing points which are produced by the section 54.

The sphygmomanometer in accordance with this particular embodiment is operated as follows:

To measure blood pressure, the switch 22 is turned on to operate the pump 34 in order to feed compressed air to the cuff 28, which is usually applied to an upper arm of a subject. After the cuff 28 has been inflated to sufficiently pressurize the upper arm, the switch 22 is turned off to deactivate the pump 34. Then, the valve 30 is opened to release the compressed air from the inflated cuff 28 at a predetermined rate for measurement, thereby sequentially lowering the pressure. While the arm is depressurized as stated, sound or oscillation produced from the blood vessel is sensed by the microphone 2 the output of which is fed to the filter and amplifier 6. The output of the filter and amplifier 6, signal K, is applied to the AD converter 12 as previously described.

Meanwhile, the varying pressure applied to the blood vessel is detected by the pressure detector 4 the output of which is coupled to the amplifier 8. The output of the amplifier 8, signal P, is also fed to the AD converter 12. The signals K and P are individually converted into digital signals at a predetermined sampling period and, then, routed to the CPU 14 which is adapted to detect Korotkoff sounds as will be described.

While the pressure exerted by the cuff 28 on the blood vessel is sequentially lowered, Korotkoff sounds appear at a certain pressure level and disappear at another pressure level which is lower than the first-mentioned one. Korotkoff sounds are detected on the basis of the signal K which is derived from the sounds which issue from the blood pressure and is detected by the microphone 2. Instantaneous cuff pressure is detected by the pressure detector 4 as pressure being applied to the blood pressure and is determined on the basis of the signal P.

In principle, the sphygmomanometer recognizes a Korotkoff sound from the signal K by means of the CPU 14 and according to a pattern recognition method, which will be described, and thereafter recognizes tailing or hangover as distinguished from the true Korotkoff sound as noise. Specifically, to distinguish the tailing of a Korotkoff sound from the Korotkoff sound, a time width is set up which is calculated using the amplitude of a Korotkoff sound recognized immediately before by a pattern recognition method, and the recognition of the following Korotkoff sound is not performed until the period of time set up expires.

The digital signal 72 which is fed from the AD converter 12 to the CPU 14 is read in by the data reading section 40 and applied therefrom to the threshold setting section 42 as a series of time-sequential waveform data 74. The threshold setting section 42 sets a threshold value in response to a signal 100 which is representative of the magnitude of a Korotkoff sound appeared immediately before, whereby the influence of noise contained in the waveform data 74 is reduced.

In detail, at the beginning of measurement, the section 42 does not set any threshold so that a signal pattern may be properly treated with no regard to its amplitude. After the start of measurement, the section 42 sets a threshold by estimating from the magnitude of a Korotkoff sound just occurred the smallest magnitude which the next Korotkoff sound may assume. That is, if Korotkoff sounds have already occurred during the measurement, the section 42 selects a particular threshold value dynamically in response to a signal 100 which is outputted by the K sound recognizing section 60 and representative of the magnitude of a Korotkoff sound. This allows the characterizing point $C_3$ to be determined accurately and rapidly.

As stated above, the threshold setting section 42 is accordance with this embodiment is different in nature from a threshold means of the prior art comparator type system, which simply sets up a fixed threshold against the varying amplitude of Korotkoff sounds. When detected waveform data greater than the threshold value set up, the section 42 delivers a detection timing signal 78 to the time generating section 46 and waveform data 80 above the threshold value to the storage 48.

The time generating section 46 comprises a unit which cyclically counts time information which is incremented on, for example, a 1 millisecond basis. In response to the timing signal 78 from the section 42, the section 46 writes time information 82 in that address of the storage 48 which bears a predetermined relation to the waveform data 80. In this manner, the waveform data 80 is written in the storage 48 together with the time information 82 of the instant when the waveform data has been detected.

Figure 7A:
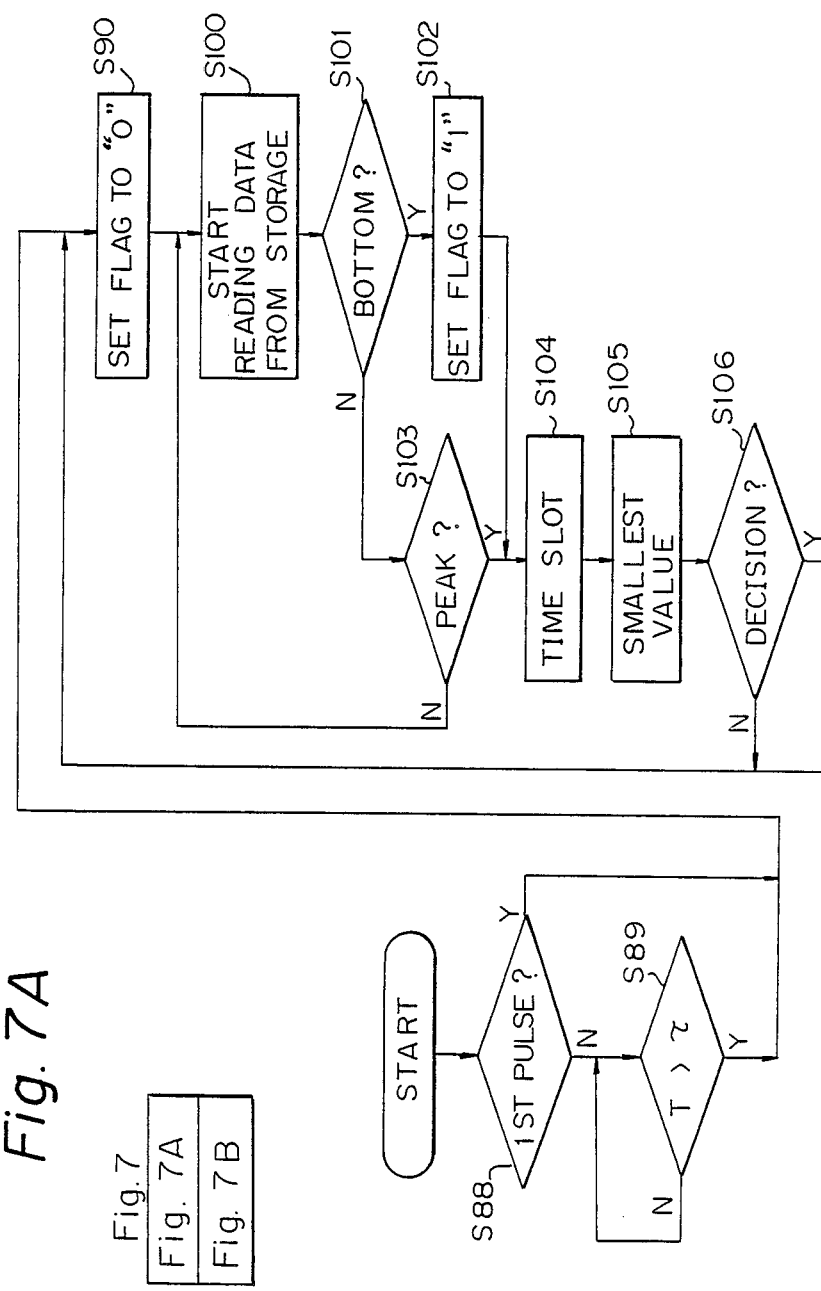
FIGS. 7A and 7B are flowcharts demonstrating a procedure for the recognition of Korotkoff sounds and the discrimination of the tailing of Korotkoff sounds.

The waveform data 80 is read out of the memory 48 by the $C_3$ detecting section 50 and the characterizing point detecting section 54 to be processed for the recognition of Korotkoff sounds. The Korotkoff sound recognition processing will be described with reference to the flowcharts of FIGS. 7A and 7B. It is to be noted that steps 88 and 89 in FIG. 7A are employed to not perform pattern recognition during a time width $\tau$ which is selected based on the amplitude of a Korotkoff sound just recognized, and will be described later.

The $C_3$ detecting section 50 sequentially examines the waveform data 84 read out of the storage 48 so as to detect the point $C_3$ of the signal pattern as shown in FIG. 3.

First, an invert flag, not shown, included in the section 50 is set to ZERO (step 90). While the invert flag is ZERO, an invert command signal 86 is reset. When the invert flag is ONE, the invert command signal 86 is set to cause the level inverting section 52 to invert the data read out of the storage 48 before passing them to the characterizing point detecting section 54. The waveform data stored in the storage 48 are sequentially read out in the order of storage (step 100) while being compared with the data 80 read out immediately before. The readout from the memory 48 can be done immediately because the data 80 are written by the threshold setting section 42.

The waveform data 80 are checked to see if an extreme value, or bottom, is present by comparing the levels of three consecutive points of the digital signal which is representative of the data (step 101). Specifically, when the differential in level between the nearby ones of the three consecutive points changes from a decrease to an increase, a characterizing point detection signal is fed to the section 54 with that point determined to be the characterizing point $C_3$. When the bottom is detected, the invert flag is set to ONE (step 102) while, at the same time, an inversion command signal 86 is delivered to the level inverting section 52. The section 52 inverts, with respect to the base line (level $P_o$ shown in FIGS. 4D and 4E), each of the levels of the waveform data 88 which are read out of the storage 48 and associated with the characterizing points $C_1$ to $C_4$, thereby providing the pattern of FIG. 3A.

If the point checked in the step 101 is not a bottom, whether or not the level differential changes from an increase to a decrease, i.e., whether or not a peak is present is decided (step 103). If a peak is not found, the program returns to the step 100 to read out the next waveform data, followed by another processing for the detection of the characterizing point $C_3$. If a peak is found, a characterizing point detection signal 92 is fed to the characterizing point detecting section 54 with the peak determined to be the characterizing point $C_3$. Thereafter, the program advances to a step 104. In this case, the invert flag is maintained ZERO.

Figure 4A:
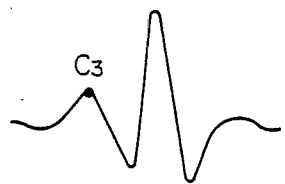
FIGS. 4A to 4O are views illustrating how discrete characterizing points are recognized by a program which is shown in FIGS. 7A and 7B.

It is the peak mentioned above that is detected first during the recognition of a Korotkoff sound. An exemplary condition in which the first peak has been detected is shown in FIG. 4A.

In response to the signal 92 from the $C_3$ detecting section 50, the characterizing point detecting section 54 starts on the detection of the consecutive characterizing points of the signal waveform which constitute a Korotkoff sound, step 104 and onward.

Figure 4B:
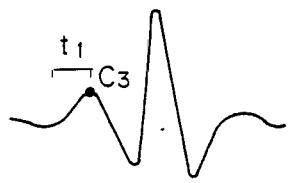

The time slot setting section 56 sets up a predetermined time slot $t_1$ the end of which is the point $C_3$, while delivering a signal 54 representative of that time slot to the K sound discriminating section 58 (step 104). The time slot $t_1$ may either be a fixed duration which is stored in a read only memory (ROM) or the like or a duration which is variable in conformity to the level of the point $C_3$. The condition in which the time slot $t_1$ is set is shown in FIG. 4B.

Figure 4C:
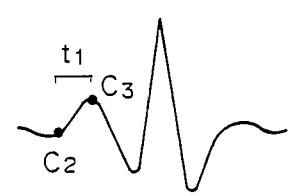
Figure 4D:
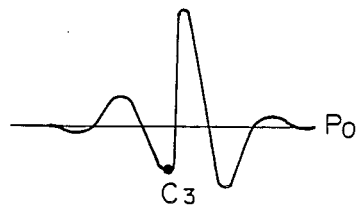

The section 58 detects the smallest one of those values which appear within the time slot $t_1$ (step 105) and determines it to be the characterizing point $C_2$ (FIG. 4C). The detection of the point of lowest level is accomplished by comparing the levels of two points of the data 90 which are outputted by the level inverting section 52. Then, whether the level differential between the points $C_2$ and $C_3$ lies within a predetermined range is decided (step 106). The upper and lower limits of the predetermined range may be stored in a ROM or the like or varied according to the interval between the points $C_2$ and $C_3$. In the exemplary condition shown in FIG. 4C, the differential between the points $C_2$ and $C_3$ does not lie in the predetermined range and, therefore, the program returns to the step 90 to repeat the detection.

Figure 4E:
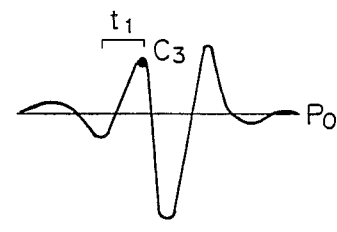
Figure 4F:
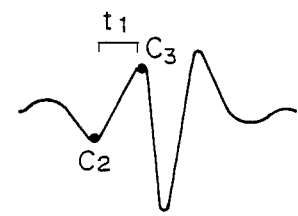

Subsequently, when a bottom is detected, the program advances from the step 101 to the step 102 where the input signal level is changed from P to $2P_o - P$ ($P_o$ = reference level), producing the waveform of FIG. 4E. This seemingly inverts the signal waveform. In the steps 104 and 105, the lowest one of those levels which appear within the time slot $t_1$ is detected (FIG. 4F).

Figure 4G:
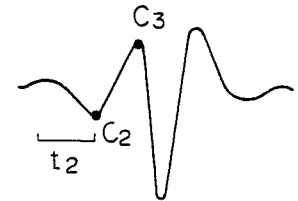

Because the level differential between the points $C_2$ and $C_3$ as decided in the step 106 this time lies in the predetermined range, the time slot setting section 56 sets up another predetermined time slot $t_2$ the end of which is the point $C_2$ (step 107) and, at the same time, delivers a time slot signal 94 too the section 58. Again, this time slot may either be a fixed one which is stored in a ROM or the like, or a one which is variable according to the level of the point $C_2$ and the level differential or the interval between the levels $C_2$ and $C_3$. FIG. 4G shows the condition in which the second time slot $t_2$ is set.

Figure 4H:
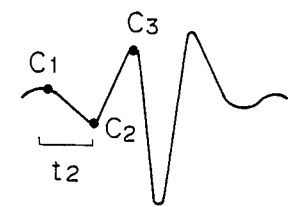

The point (value) at which the highest level has been detected in the time slot $t_2$ is determined to be the point $C_1$ (step 108). The signals representative of the detected points $C_3$, $C_2$ and $C_1$ are stored in the RAM. The highest level is detected by comparing the levels of two points. Whether or not the level differential between the points $C_1$ and $C_2$ lies in a predetermined range is decided (step 109). Again, the upper and lower limits of this range may be stored in a ROM or varied each time in accordance with the interval between $C_1$ and $C_2$ and the level difference and interval between $C_2$ and $C_3$. In this particular example, the detection of $C_1$, $C_2$ and $C_3$ as shown in FIG. 4H is decided inadequate, so that the program returns to the step 90.

Figure 4I:
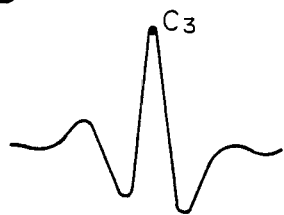
Figure 4J:
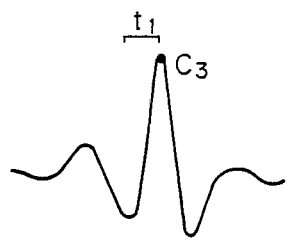
Figure 4K:
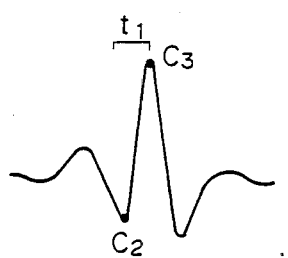
Figure 4L:
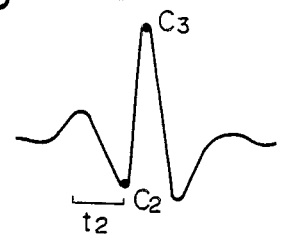
Figure 4M:
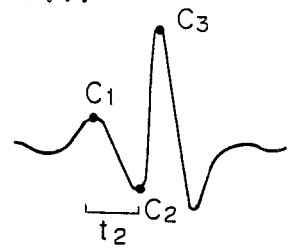

Next, the point $C_3$ shown in FIG. 4I is detected as a characterizing point. Then, the time slot $t_1$ is set up as shown in FIG. 4J (step 104). After the detection of a characterizing point $C_2$ as shown in FIG. 4K (step 105), another time slot $t_2$ is set up the end of which is the point $C_2$ (step 107) and, then, the highest level $C_1$ within the time slot $t_2$ is detected (step 108), as shown in FIG. 4M. In the following step 109, the detection of the points $C_1$, $C_2$ and $C_3$ is decided adequate. The program now advances to a step 110.

Figure 4N:
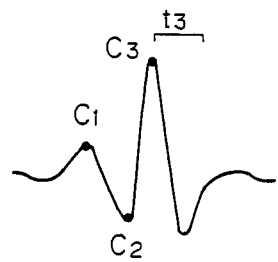
Figure 4O:
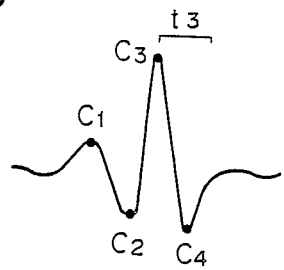

In the step 110, the time slot setting section 56 sets a third time slot $t_3$ the beginning of which is the point $C_3$, as shown in FIG. 4N. This time slot $t_3$ may be a fixed value which is stored in a ROM, or a value which is variable based on the level differential or the interval between $C_1$ and $C_2$ and that between $C_2$ and $C_3$. The point of lowest level which is detected within the time slot $t_3$ is determined to be the characterizing point $C_4$ (step 111). The resultant condition is shown in FIG. 4O. Thereafter, whether or not the level differential between the points $C_3$ and $C_4$ is included in a predetermined range is determined (step 112). The upper and lower limits of this particular range may be stored in a ROM or varied based on the interval between the points $C_3$ and $C_4$, or the level difference or the interval between the points $C_1$ and $C_2$ or that between the points $C_2$ and $C_3$. When the level differential determined is not included in the predetermined range, the program returns to the step 90 again. When it is included in the predetermined range, that Korotkoff sound has occurred is recognized (step 113).

It is to be noted that the K sound recognizing section 60 comprises a set of conditional propositions for examining the positional relationship between the four characterizing points $C_1$ to $C_4$ which are determined by the section 54, as stated above. Such conditional propositions are open to choice.

As described above, pattern recognition in accordance with this embodiment directly examines the characteristic of a Korotkoff sound waveform. This eliminates the need for a limitation heretofore placed on the frequency band characteristic of a filter, and the need for a fixed threshold value against the varying amplitude of Korotkoff sounds. In addition, the accuracy of measurement is hardly susceptible to the difference in the frequency component and amplitude which constitute Korotkoff sounds.

Figure 5:
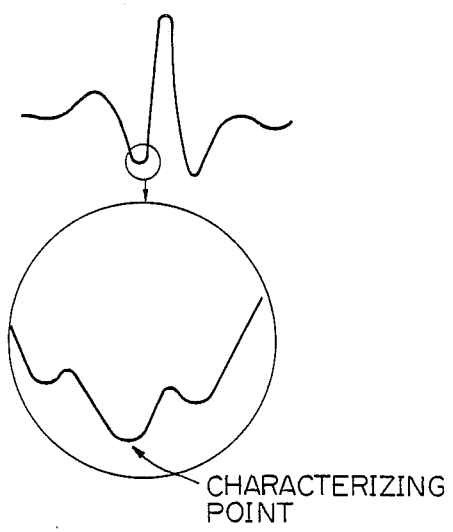
FIG. 5 is a view showing a Korotkoff sound waveform in which fine ripples are appearing in the vicinity of an extreme value.

The embodiment shown and described is not such that all of the maximum and minimum values are detected by simply tracing a wave-form, but such that the largest and smallest ones of extreme values are detected which the constituent parts of a Korotkoff sound may assume within each of discrete time slots. Hence, detection of estimated characterizing points can be readily implemented with a short program, and the accuracy of measurement is free from the influence of fine ripples which occur in the vicinity of extreme values of a Korotkoff sound waveform, as shown in FIG. 5, especially those apt to result from conversion errors after AD conversion.

Furthermore, the recognition method in accordance with this embodiment is advantageous in that a plurality of signal patterns of Korotkoff sounds can be recognized efficiently on a real time basis by simple software which is programmed to recognize typical patterns of Korotkoff sound waveform, and in a limited storage and processing time available with a one-chip CPU. Especially, the level inverting means facilitates the recognition of a plurality of patterns with a short program.

While the embodiment has been shown and described as inverting, according to requirement, each of the peak and bottom of a signal waveform which are the reference characterizing points for recognition, they may be processed without being inverted or, alternatively, only the peak of a waveform may be used as a reference characterizing point. In such a case, the invert flag and the level inverting section 52 are needless.

Hereinafter will be described an operation for excluding the tailing of a Korotkoff sound which constitutes noise.

Figure 6:
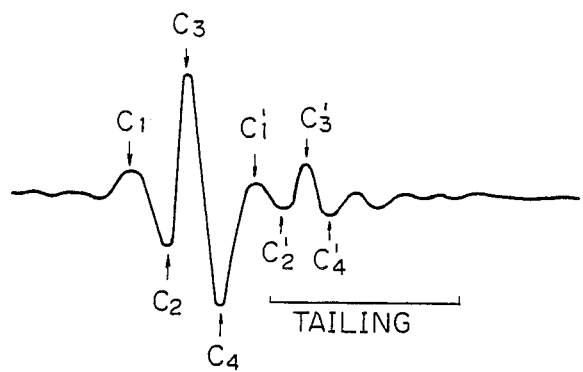
FIG. 6 is a view representative of the tailing of Korotkoff sound.

As shown in FIG. 6, a Korotkoff sound is followed by a waveform pattern which is smaller in amplitude than but similar to a Korotkoff sound, i.e. tailing of a Korotkoff sound. In FIG. 6, $C'_1$, $C'_2$, $C'_3$ and $C'_4$ are representative of characterizing points which would undesirably allow the tailing of a Korotkoff sound to be recognized as true Korotkoff sound. The procedure which will be described is used to prevent the tailing from being recognized as Korotkoff sound.

Figure 7B:
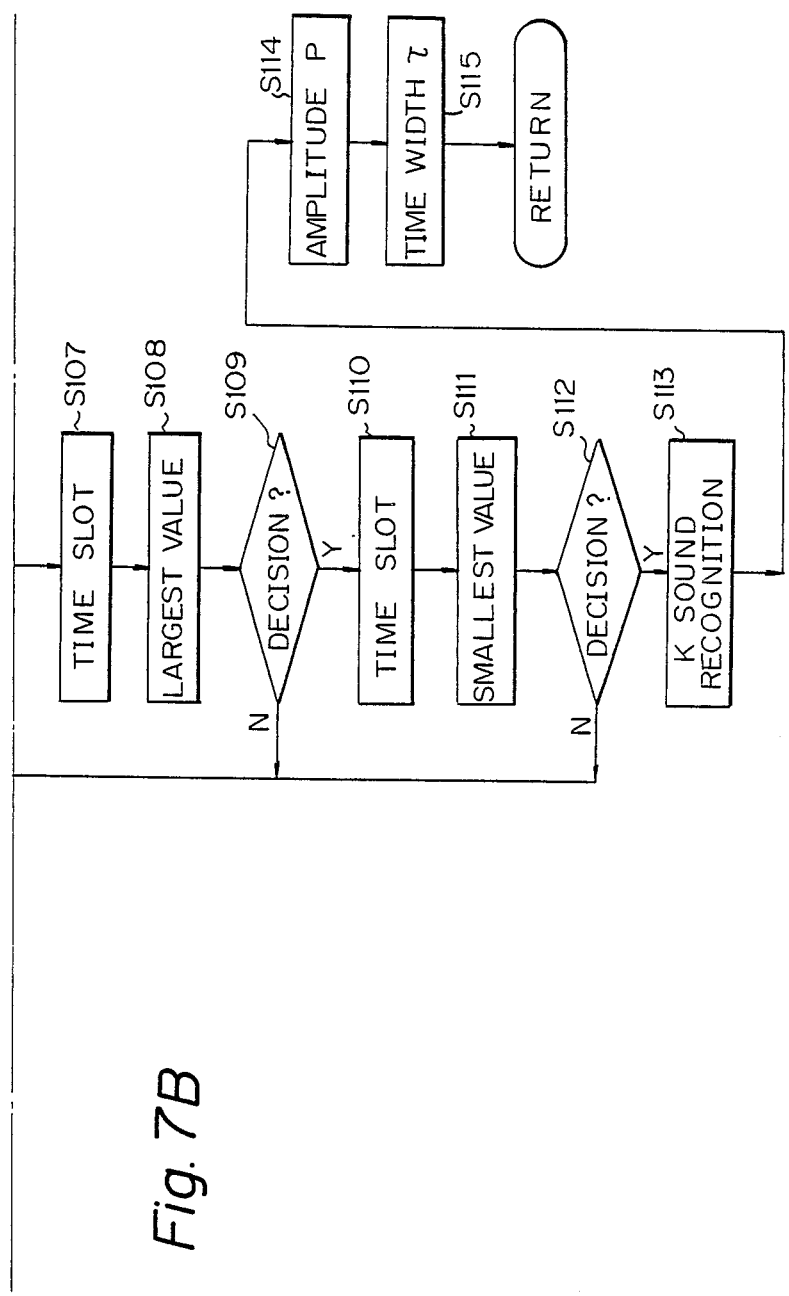

After the recognition of Korotkoff sound as performed in the step 113 of FIG. 7B, the amplitude P of the Korotkoff sound is calculated based on the characterizing points $C_1$, $C_2$, $C_3$ and $C_4$ (step 114). For the calculation of P, any of the following equations may be used:

$$P = P_3 - P_2 \qquad \text{Eq. (1)}$$

$$P = P_3 - P_4 \qquad \text{Eq. (2)}$$

$$P = P_3 - \min(P_2, P_4) \qquad \text{Eq. (3)}$$

where $P_2$, $P_3$ and $P_4$ are respectively representative of the levels of a waveform at the characterizing points $C_2$, $C_3$ and $C_4$.

The Eqs. (1), (2) and (3) respectively produce as the amplitude P the difference between $P_2$ and $P_3$, the difference between $P_3$ and $P_4$, and the difference between $P_3$ and smaller one of $P_2$ and $P_4$. It should be noted, however, that the above equations are only illustrative and may be replaced with any other desired one.

Subsequently, a time width $\tau$ is set up on the basis of the amplitude P of a Korotkoff sound calculated (step 115). The time width $\tau$ is a period of time during which the tailing of a Korotkoff sound is assumed to occur, and employed to prevent the tailing from being recognized as Korotkoff sound after the latter has been recognized. In this particular embodiment, recognition of Korotkoff sounds is inhibited until the time $\tau$ expires since the recognition of a Korotkoff sound.

Several different approaches may be contemplated for the selection of the time width $\tau$, as exemplified by the following equations:

$$\tau = \alpha P \qquad \text{Eq. (4)}$$

$$\tau = P + \alpha \qquad \text{Eq. (5)}$$

$$\tau = \alpha P + \beta \qquad \text{Eq. (6)}$$

As regards $\alpha$ and $\beta$ adapted to eliminate omission of recognition due to the time width $\tau$, they may be stored in a ROM or like storage or varied in accordance with the interval between $C_1$ and $C_2$ and that between $C_2$ and $C_3$.

The Eqs. (4), (5) and (6) produce the time width $\tau$ as a value proportional to the amplitude P of a Korotkoff sound, a value which is the sum of the amplitude P and a predetermined value, and a value which is the sum of a value proportional to the amplitude P and a predetermined value, respectively.

As stated above, after the recognition of a Korotkoff sound, a time width $\tau$ is set up based on its amplitude. It should be born in mind that the amplitude of a Korotkoff sound upon which the time width $\tau$ is dependent as described above is not restrictive and may be replaced with any of other suitable factors.

Turning back to FIG. 7A, the procedure for distinguishing the tailing of a Korotkoff sound from true Korotkoff sound before pattern recognition begins at a step 88. In the step 88, whether or not the Korotkoff sound to be recognized is the first one ever occurred. If it is the first sound, the program advances to the step 90 to enter into the previously described pattern recognition without executing the tailing removal processing. If it is not the first one, the time interval T between the occurrence of a Korotkoff sound recognized immediately before and the present time is compared with the time width $\tau$ which has been set in the step 115, so as to see if T is greater than $\tau$ (step 89). If T is greater than $\tau$, the operation is transferred to the step 90. If T is not greater than $\tau$, the program waits until T becomes greater than $\tau$ and, then, advances to the step 90. The time interval T may be set as follows:

$$T = t - t_4$$

$$T = t - t_3$$

where t denotes the present time, and $t_3$ and $t_4$ denote, respectively, the times at which the characterizing points $C_3$ and $C_4$ of a Korotkoff sound recognized immediately before are detected. Hence, the time interval T is representative of a period of time between the time when the characterizing point $C_3$ or $C_4$ of a Korotkoff sound recognized immediately before was detected and the present time. Using as the time interval T the period of time between the time $t_1$ or $t_2$ at which the point $C_1$ or $C_2$ was detected and the present time is not desirable because the times $t_1$ and $t_2$ are unsuitable as the points of Korotkoff sound recognition.

In accordance with this embodiment, the time width $\tau$ in which the tailing of a Korotkoff sound is assumed to occur is set up so that the recognition of a Korotkoff sound may not be effected until the time interval T between a Korotkoff sound recognized immediately before and the present time exceeds the time $\tau$. This prevents the tailing from being erroneously taken for a Korotkoff sound and, thereby, effectively removes noise which is contained in the tailing and similar in wave-form to a Korotkoff sound. Moreover, because the time width $\tau$ is selected on the basis of the amplitude of a Korotkoff sound recognized, it becomes wider when the amplitude of Korotkoff sound and, therefore, the tailing is great. It follows that even if the tailing is varied in length with the amplitude of a Korotkoff sound, it is surely distinguished from a Korotkoff sound. Conversely, when the amplitude is small, the time width $\tau$ becomes narrower eliminating omission of recognition of the next Korotkoff sound.

Figure 8:
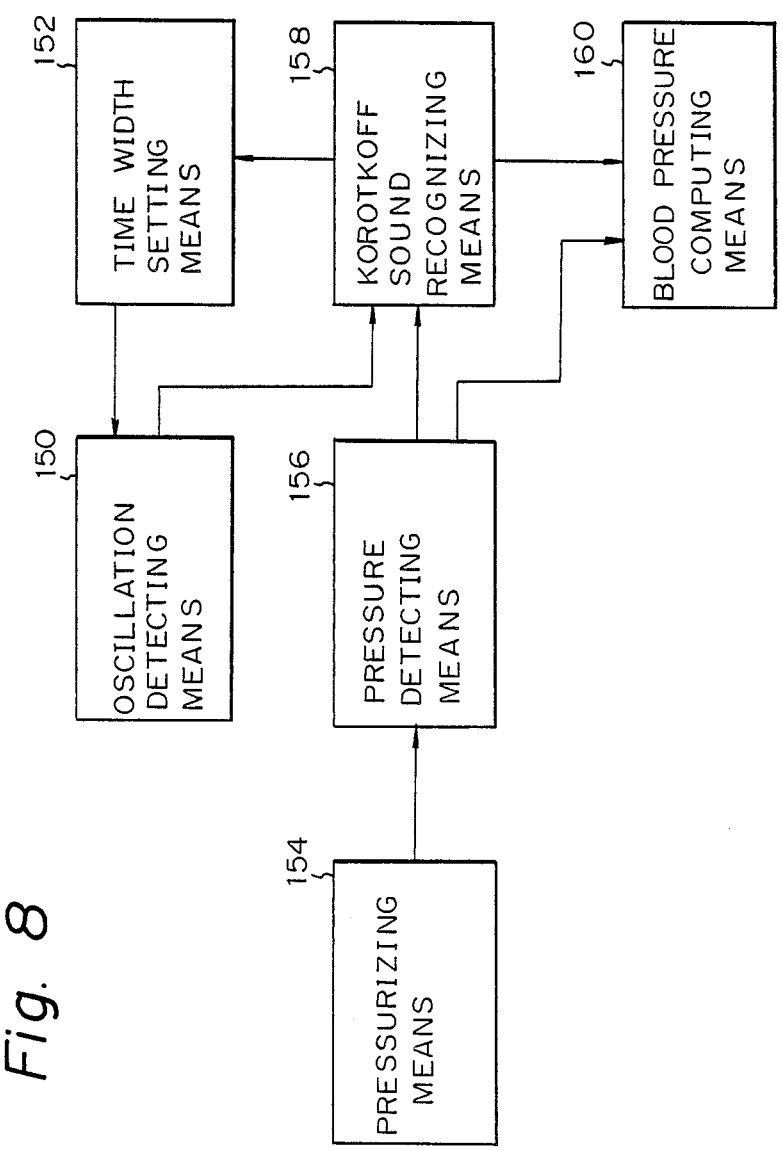
FIG. 8 is a block diagram showing the general construction of the sphygmomanometer in accordance with the present invention.

Referring to FIG. 8, the sphygmomanometer in accordance with the present invention is shown in a generalized block diagram. As shown, it comprises a pressurizing means 154, a pressure detecting means 156, a Korotkoff sound recognizing means 158, an oscillation detecting means 150, a time width setting means 152, and a blood pressure computing means 160. The pressurizing means 154 varies the pressure which is applied to a blood vessel while, at the same time, the pressure detecting means 156 detects the pressure being applied to the blood vessel. Oscillation of the blood vessel being compressed by the means 154 is sensed by the oscillation detecting means 150, and Korotkoff sounds are recognized by the Korotkoff sound recognizing means 158 out of the oscillation sensed. When the means 158 has recognized Korotkoff sound, the computing means 160 computes blood pressure of a subject from the pressure which is detected by the means 156. The time width setting means 152 sets up a certain time width based on the Korotkoff sound which is recognized by the means 158, so that the output of the means 150 may not be fed to the means 158 until that time width expires.

As stated above, because a time width $\tau$ which matches with a particular length of tailing of a Korotkoff sound so as to inhibit recognition of Korotkoff sounds during the period of time $\tau$, the tailing is prevented from being erroneously recognized as a Korotkoff sound. Such further promotes the accuracy of Korotkoff sound.

While the present invention has been described with reference to the particular illustrative embodiment, it is not to be restricted by that embodiment but only by the appended claims. It is to be appreciated that those skilled in the art can change or modify the embodiment without departing from the scope and spirit of the present invention.

What is claimed is:

1. A sphygmomanometer, comprising:
   pressurizing means for applying variable pressure to a blood vessel;
   oscillation detecting means for detecting oscillation produced from the blood vessel while pressurized by said pressurizing means;
   pressure sensing means for sensing pressure being applied to the blood vessel;
   Korotkoff sound recognizing means for recognizing Korotkoff sounds out of the oscillation detected by said oscillation detecting means;
   blood pressure computing means for computing blood pressure from the pressure applied to the blood vessel as detected by said pressure detecting means when said Korotkoff sound recognizing means has recognized one of the Korotkoff sounds; and
   time width setting means for setting a delay period of time based on the amplitude of a most recent one of the Korotkoff sounds recognized by said Korotkoff sound recognizing means and for inhibiting an output from said oscillation detecting means to said Korotkoff sound recognizing means during the delay period, thereby said Korotkoff sound recognizing means being unable to recognize any of the Korotkoff sounds until the delay period of time set by said time width setting means expires.

2. A sphygmomanometer in accordance with claim 1, wherein said Korotkoff sound recognizing means comprises:
   signal waveform holding means for holding a signal waveform detected by said oscillation detecting means,
   maximum and minimum point detecting means for detecting a maximum point $C_3$ of the signal waveform held in said signal waveform holding means and for detecting a first point of smallest value $C_2$ lying in a first predetermined time slot $t_1$ ending with the maximum point $C_3$, and
   level differential deciding means for deciding whether a first level differential between the first point of smallest value $C_2$ and the maximum point $C_3$ lies within a first predetermined range, wherein
   when said level differential deciding means determines that the first level differential lies in the first predetermined range, said maximum and minimum point detecting means detects a point of largest value $C_1$ lying in a second predetermined time slot $t_2$ ending with the first point of smallest value $C_2$ and said level differential deciding means decides whether a second level differential between the second point of largest value $C_1$ and the first point of smallest value $C_2$ lies in a second predetermined range,
   when said level differential deciding means determines that the second level differential lies in the second predetermined range, said maximum and minimum point detecting means detects a third point of smallest value $C_4$ lying in a third predetermined time slot $t_3$ beginning with the maximum point $C_3$ and said level differential deciding means decides whether a third level differential between the third point of smallest value $C_4$ and the maximum point $C_3$ lies in a third predetermined range, and
   when said level differential deciding means determines that the third level differential lies within the third predetermined range, said Korotkoff sound recognizing means thereby recognizes that one of the Korotkoff sounds is contained in the signal waveform.

3. A sphygmomanometer in accordance with claim 2, wherein said maximum and minimum point detecting means detects the maximum point of the signal waveform held in said signal waveform holding means by comparing values at three points of the signal waveform.

4. A sphygmomanometer in accordance with claim 3, wherein said Korotkoff sound recognizing means further includes inverting means for inverting the signal waveform held in said signal waveform holding means when a minimum point is detected in the signal waveform, said inverting means inverting the signal waveform before the maximum point is detected by said maximum and minimum point detecting means.

5. A method of detecting blood pressure comprising the steps of:
  (a) applying variable pressure to a blood vessel;
  (b) detecting oscillation produced from the blood vessel pressurized in step (a);
  (c) recognizing Korotkoff sounds out of the oscillation detected in step (b);
  (d) sensing pressure being applied to the blood vessel when said Korotkoff sound has been recognized in step (c);
  (e) computing blood pressure from the pressure applied to the blood vessel detected in step (d);
  (f) setting a period of time based on the amplitude of a most recent one of the Korotkoff sounds recognized in step (c); and
  (g) preventing said recognizing of the Korotkoff sounds in step (c) during the period of time set in step (f).

6. A method in accordance with claim 5, wherein said recognizing the Korotkoff sounds in step (c) includes the substeps of:
  (ci) holding a signal waveform detected in step (b),
  (cii) detecting a maximum point $C_3$ of the signal waveform,
  (ciii) detecting a first point of smallest value $C_2$ lying in a first predetermined time slot $t_1$ ending with the maximum point $C_3$,
  (civ) deciding whether a first level differential between the first point of minimum value $C_2$ and the maximum point $C_3$ lies within a first predetermined range,
  (cv) detecting a second point of largest value $C_1$ lying in a second predetermined time slot $t_2$ ending with the second point of smallest value $C_2$ when a first decision is made in step (civ) that the first level differential lies in the first predetermined range,
  (cvi) deciding whether a second level differential between the second point of largest value $C_1$ and the first point of smallest value $C_2$ lies in a second predetermined range,
  (cvii) detecting a third point of smallest value $C_4$ lying in a third predetermined time slot $t_3$ beginning with the maximum point $C_3$ when a second decision is made in step (cvi) that the second level differential lies in the second predetermined range, and
  (cviii) deciding whether a third level differential between the third point of smallest value $C_4$ and the maximum point $C_3$ lies in a third predetermined range.

7. A method in accordance with claim 6, wherein said detecting the maximum point in the signal waveform in step (cii) includes comparing values at three points of the signal waveform.

8. A method in accordance with claim 7, wherein said recognizing of the Korotkoff sounds in step (c) further includes the step of (cix) inverting the signal waveform held in step (ci) when a minimum point is detected out of the signal waveform before the maximum point is detected.

* * * * *